United States Patent [19]

Allison et al.

[11] Patent Number: 4,928,709

[45] Date of Patent: May 29, 1990

[54] CERVICAL RANGE OF MOTION MEASURING DEVICE

[75] Inventors: John D. Allison, Shoreview; Gordon Hanson, Roseville, both of Minn.

[73] Assignees: Regents of the University of Minnesota, Minneapolis; Performance Attainment Associates, Inc., Roseville, both of Minn.; a part interest

[21] Appl. No.: 186,795

[22] Filed: Apr. 27, 1988

[51] Int. Cl.$^5$ .............................................. A61B 5/10
[52] U.S. Cl. ................................. 128/782; 33/355 R; 33/512
[58] Field of Search ....................... 128/774, 781, 782; 33/345, 355, 358, 511, 512, 515

[56] References Cited

U.S. PATENT DOCUMENTS

| | | | |
|---|---|---|---|
| 237,939 | 2/1881 | Wilson | 600/15 |
| 1,590,499 | 6/1926 | Cozad | 33/512 |
| 2,491,312 | 12/1949 | Henry et al. | 33/200 |
| 2,501,745 | 3/1950 | Sherman | 33/88 |
| 2,565,381 | 8/1951 | Leighton | 33/221 |
| 2,677,894 | 5/1954 | Belgard | 33/200 |
| 3,429,052 | 2/1969 | Hembd et al. | 33/220 |
| 3,614,950 | 10/1971 | Rabey | 128/2 R |
| 4,279,260 | 7/1981 | Stump | 128/774 |
| 4,328,620 | 5/1982 | Mack et al. | 33/174 D |
| 4,444,204 | 4/1984 | Bryant et al. | 128/781 |
| 4,485,825 | 12/1984 | Domjan et al. | 128/774 |
| 4,528,990 | 7/1985 | Knowles | 128/782 |
| 4,586,515 | 5/1986 | Berger | 128/782 |
| 4,587,956 | 5/1986 | Griffin et al. | 600/15 |
| 4,777,965 | 10/1988 | Allison et al. | 128/781 |

FOREIGN PATENT DOCUMENTS

| | | |
|---|---|---|
| 3317918 | 6/1984 | Fed. Rep. of Germany . |
| 3525756 | 12/1986 | Fed. Rep. of Germany ....... 128/781 |
| 1534545 | 7/1968 | France . |

OTHER PUBLICATIONS

*Professional Health Care Catalog*, Fred Sammons, Inc. (1985).
O'Driscoll, Susan L. et al., "Neck Movements in Ankylosing Spondylitis and Their Responses to Physiotherapy", *Annals of the Rheumatic Diseases*, 1978, vol. 37, pp. 64–66.
Brochure entitled "'Myrin' Goniometer", LIC Rehab Care, Solna, Sweden.
Kadir, N. et al., "A New Neck Goniometer", *Rheumatology and Rehabilitation*, 1981, vol. 20, pp. 219–226.
O'Riain, Micheal D., Ph.D., "Report of Projects Completed May 1981–1983", Royal Ottawa Hospital (1983).
Weiss, Marian, M.D., "A Multiple Purpose Goniometer", *Archives of Physical Medicine & Rehabilitation*, Konstancin, Poland, Apr. 1964, pp. 197, 198.
"An Experimental Study of Head Motion in Adult Males", *Journal of the American Physical Therapy Association*, Mar. 1964, vol. 44, No. 3, pp. 163–165.

*Primary Examiner*—Randall L. Green
*Assistant Examiner*—Randy Shay
*Attorney, Agent, or Firm*—Kinney & Lange

[57] ABSTRACT

A device and process for measuring cervical range of motion about three axes comprises a frame which is supported on the nose of a subject and which has side temple pieces for locating the frame on the wearer's head. Cervical range of motion of a wearer's head can be measured through the use of gravity type angle meters and a magnetic type angle meter which are mounted on the frames and easily referenced back to the frame. The magnetic type angle meter is mounted above the head on a removable arm, which is supported on the frame. A magnetic field is created using magnets mounted on the subject to obtain reliable head rotation readings. The magnetic type angle meter can be removed, and an arm which is mounted on the frame and extends above the head of a wearer and which when coupled with a locator arm can determine a forward head position measurement.

22 Claims, 4 Drawing Sheets

CERVICAL RANGE OF MOTION MEASURING DEVICE

This invention was made at least in part with government support under Grant No. G008300075 awarded by the National Institute of Handicapped Research of the Department of Education. The government has certain rights in this invention.

BACKGROUND OF THE INVENTION

1. Field of the Invention

This invention relates to a device and related Process for measuring the range of cervical motion of a patient about three axes of rotation, and forward head posture.

2. Description of the Prior Art.

Several devices have been used to measure the range of cervical motion. Typically, such devices have utilized an angle finder and/or compass detachably secured to the human body through the use of a belt or strap to obtain the necessary measurements.

U.S. Pat. No. 4,485,825 to Domjan et al. discloses what is referred to as an arthrospinometer having an inclinometer and a north-south-seeking compass carried in a housing pivotally mounted on a base plate. The base plate has a scale thereon and an indicator is provided for indicating on the scale the degree of rotation relative to the base plate. There is also a scale for indicating the amount of rotation of the inclinometer and compass relative to the housing and this scale is rotatable relative to the housing about a common third axis. The base plate has a suction cup attached to its bottom side in order to secure the device to a portion of the human body. Such a method of securing the device to the human body does not facilitate the making of reproducible measurements as standardized placement and positioning are difficult.

The "Myrin" Goniometer produced by LIC Rehab Care utilizes an inclination needle and compass to indicate degree of rotation. The Myrin Goniometer is strapped to the body to take readings about a variety of joints. Reproducibility of data is very difficult as there are no established reference landmarks. Also, the Myrin Goniometer does not allow precise orientation of the inclination needle and compass as only the strap is used in mounting, making standardized measurements very difficult to reproduce for an objective comparison.

Other devices have been designed for measuring the range of cervical motion. In particular, U.S. Pat. No. 2,565,381 to Leighton discloses a device having a weighted pointer mounted within a housing having a rotatable calibrated dial. The device is attached to the body on one side of a joint and the weighted pointer is used to measure range of motion about the joint. U.S. Pat. No. 3,429,052 to Hembd et al. discloses a similar device which is dampened to reduce the oscillation of the weighted pointer which occurs in the Leighton device. Neither of these devices permits the making of range of motion measurements in more than one plane without having to reattach the device at a new position on the body. In addition, the data obtained would likely not be reproducible as no predesignated landmarks are established.

Other methods used for obtaining range of motion measurements have used a more mechanical approach. For example, U.S. Pat. No. 1,590,499 to Cozad discloses a device which may be attached to a human arm across the elbow as the arm is flexed or extended. Range of motion measurements are taken through the use of a protractor mounted on the device and a pointer which moves relative to the movement of the arm. Devices of this type are difficult to use in obtaining objective range of cervical motion measurements. Also, such mechanical devices are not conducive to obtaining reproducible data concerning range of cervical motion.

Various devices have been mounted on eyeglass type frames in order to obtain vision related measurements. For example, U.S. Pat. Nos. 2,491,312 to Henry et al. and 2,677,894 to Belgard disclose devices for taking ophthalmic measurements. The devices are designed to take measurements which facilitate the proper positioning of an eyeglass lens in front of the pupil. Such devices are of particular value to those patients wearing bifocal lenses. U.S. Pat. No. 4,328,620 to Mack et al. discloses a device which utilizes an eyeglass type frame to properly position an apparatus which registers the movements of the lower jaw with reference to the skull. The Mack device, however, is not capable of obtaining range of cervical motion measurements.

U.S. Pat. No. 4,586,515 to Berger shows a system for measuring motion in three dimensions, and U.S. Pat. No. 2,501,745 to Sherman shows a device for measuring angular movements including a level assembly for indicating a level condition.

Additional art of interest includes the following:

| Country | Patent No. | Inventor |
| --- | --- | --- |
| U.S. | 3,614,950 | Rabey |
| U.S. | 4,279,260 | Stump |
| U.S. | 4,528,990 | Knowles |
| U.S. | 4,444,204 | Bryant et al |
| Germany | 3317918 | Gross |
| France | 1534545 | Kurose |

Cervical region pathology is a common problem in humans with the instance increasing with age. A major symptom or sign of pathology is loss of motion in one or more planes of movement, and associated pain. Measurement of cervical motion of patients during the course of a therapeutic regimen provides objective data on the benefits of the selected treatment approach. Standardization of a protocol for measuring the motions of flexion/extension, lateral or side bending and rotation, and head and neck posture is a prerequisite to satisfactory use of objective and comparative measurements of cervical range of motion, which in turn permits objective evaluation of the theraputic regime.

An added feature is the adaptation that allows for measuring forward head posture. The therapeutic intervention is direct and correcting abnormalities restores limited motion, and also restores a more normal postural alignment.

SUMMARY OF THE INVENTION

The present invention comprises embodiments to permit objectively measuring the range of cervical motion of a patient, particularly when the disclosed process is used. Objective and comparative measurements are taken by mounting the measurement device in a reference position using known reference points on the patient's head. Proper positioning is achieved according to the present invention in that an adjustable frame similar to an eyeglass frame is used to mount the motion measuring device to the patient's head. The frame is supported with a nose pad which when used with a pair of temples or bows supported on the ears, provides repeatable reference positioning. The temple pieces have an adjustable strap which wraps around the back of the head in order to secure the eyeglass frame to the head following proper positioning. The bridge of the nose and the tops of the ears establish reference points which permit the frame to be quickly mounted and used.

Measurements of the range of cervical motion are obtained according to the invention through the use of angle meters. Gravity type angle meters are used for measuring angles about horizontal axes and a magnetic type angle meter is used for determining angles about a vertical axis.

The gravity type angle meter comprises a pendulum pivotally mounted on a horizontal axis relative to a vertical case that adjusts to gravitational change. The magnetic type angle meter is a magnetic needle-compass type instrument. Lateral or side bending movement of the head and cervical spine are recorded with a gravity type angle meter in the coronal or frontal plane. The sagittal axis of one gravity type angle meter extends fore and aft and the gravity type angle meter is mounted ahead of the forehead of a subject. The cervical spine and suboccipital flexion/extension measurements are taken with a gravity type angle meter measuring angles in the sagittal plane (a vertical fore and aft plane bisecting the body). The gravity type angle meter is mounted on the side of the temple of a subject with the axis oriented transversely (frontal or coronal axis) for these measurements.

Rotational readings about a generally vertical axis are taken from the magnetic type gravity meter.

The frame, the nose bridge and the temple pieces or bows are thermally formed from one piece of plastic. Distinct hinge pins for the bows or temples are not required, but the frame provides a flexion hinge-type frame to fit different head sizes.

The earth's magnetic field is usually at least partially shielded and unreliable in examination facilities. In the present invention, a magnetic field alignment device is placed over the shoulders of a subject with a harness, and is used to establish a reliable magnetic field for making accurate, repeatable measurements with the magnetic type angle meter. Magnets are placed both on the front and rear of the subject, for establishing this field.

A support arm for the magnet goniometer which measures rotation of the head is attached to the front frame of the device and extends upwardly and rearwardly over the top of the head. The arm can be replaced with a second arm that is used for making forward head position measurements. The measurements are made with a reference locator bar held vertically and in contact with a selected vertabrae to establish the reference measurement.

DESCRIPTION OF THE PREFERRED EMBODIMENTS

An eyeglass type frame assembly 60 used for measuring range of cervical motion about three axes of rotation supports three angle meters or goniometers, on a subject 59, for measuring angles in the frontal, sagittal, and horizontal planes, respectively. The eyeglass type frame 60 is a flexible, formed plastic frame that utilizes precison molded plastic parts in key areas to facilitate (i) interchanging a support arm used for holding the head rotation measurement angle finder with a forward-head measuring arm that provides a structure for accurately measuring the forward-head position of a subject, and (ii) a precision meter mount for easily positioning an angle meter.

The frame assembly 60 is accurately and reliably positioned on the subject with a nose piece comprising replaceable, soft plastic nose pad 61. The nose pad and the two ear bows provide reference members for positioning the frame assembly on the bridge of the nose and the tops of the ears which are the reference locations for repeatable positioning. The frame assembly 60 includes a front cross frame 62 (see FIG. 2) and temple pieces or bows 63.

Figure 1:
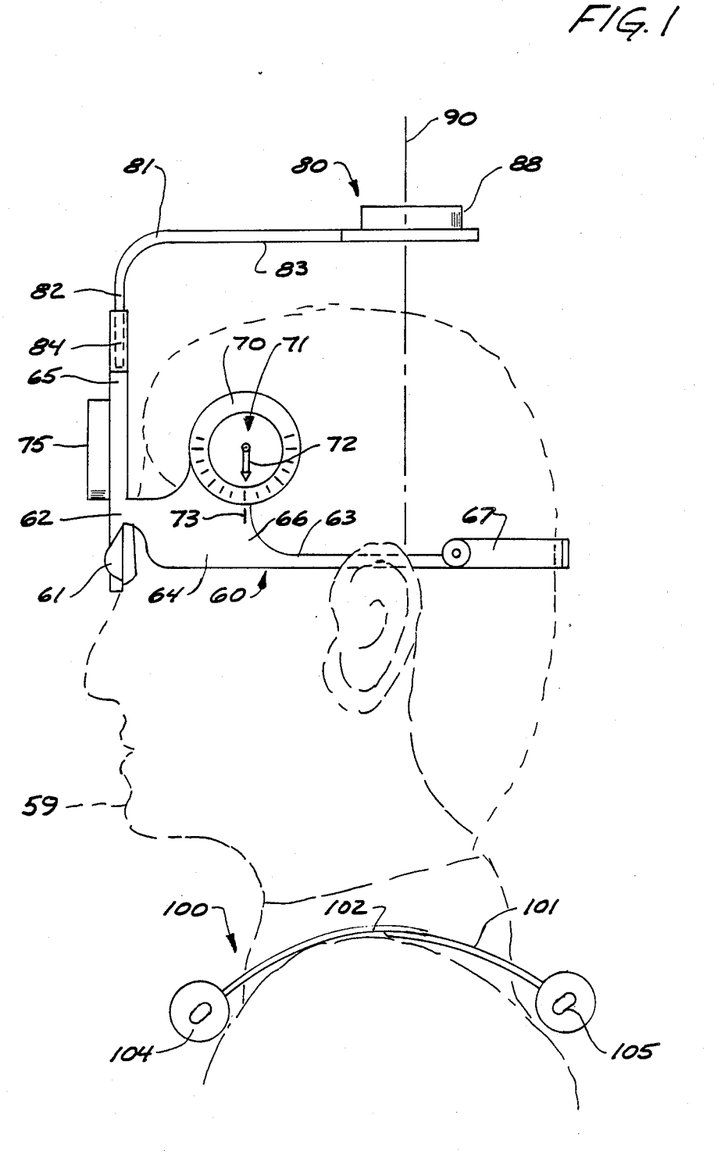
FIG. 1 is a left side elevational view of a device used for measuring cervical motion shown in place on a subject with gravity angle meters for measuring flexion and extension in the sagittal plane illustrated thereon.

The front frame 62 and bows are somewhat flexible, thermo-formed plastic, and the bows are capable of hinging relative to the front frame 62. The front frame 62 extends laterally across the forehead. A side support plate 64 is an integral part of the left bow 63 adjacent to the temple of a subject. The support plate 64 is securely mounted with respect to the front frame 62, so that the plane of the side support plate 64 shown in FIG. 1 is substantially at right angles to the plane of an upright front arm support 65 that extends upwardly from the front cross frame in the center thereof, above the nose pad. The bow 63 on the left side of the frame assembly will flex at the junction area indicated at 66 between the front cross frame 62 and the side support plate 64. The bow 63 on the opposite side of the frame assembly also will hingedly flex relative to the front cross frame.

The bows 63 rest on the ears of the subject and have suitable strap sections 67,67 fixed to the rear ends thereof. The outer ends of the strap sections can be adjustably fastened together with hook and loop fasteners sold under the trademark VELCRO to hold the frame assembly 60 securely on the subject's head. Plastic screws pass through eyelets in the strap sections 67 to attach the strap sections to the bows, while allowing the strap sections to move smoothly with respect to the bows.

The replaceable molded nose pad 61 is relatively soft and allows for accurate, comfortable, and reliable positioning on different nose and forehead structures.

Fluid damped gravity type angle meters are used for measuring the sagittal plane flexion and extension of the neck (nodding motion), and the lateral flexion of the neck in the frontal plane.

When the frame assembly 60 is manufactured, a gravity-type angle meter 71 is mounted in an outer support ring 70 that is unitary with the side support plate 64. The angle meter 71 includes an angle indicating pendulum needle 72 that is weighted to point downwardly under gravity. During manufacturing, a scribe mark 73 is placed on the support plate 64 and is used to position the angle meter zero scale before cementing the ring 70 in place. Then, the angle meter 71 is fixed in position on ring 70 so that it will always have the same reference position relative to the nose and ears. This fixed zero assures the same reference point will be available in all future measurements insofar as the sagittal plane flexion and extension measurements of the subject are concerned. Whenever the needle of angle meter 71 indicates zero (when it aligns with the scribe mark), the axes of the bows are horizontal.

Figure 2:
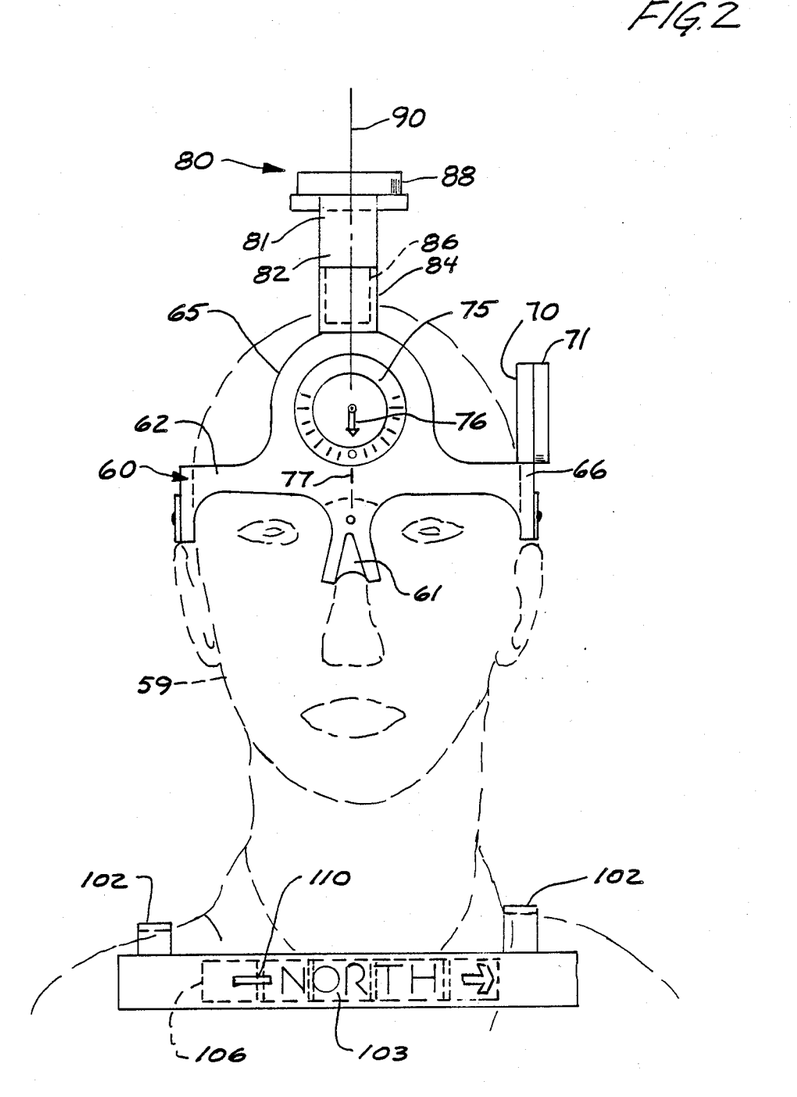
FIG. 2 is a front elevational view of the device of FIG. 1, showing a gravity type angle meter for measuring lateral motion of the head in front view.

The upright front support 65 mounts a second gravity type angle meter 75, for measuring the lateral flexion of the neck. This angle meter 75 is mounted for measuring angles in the frontal plane above the nose pad 61. The gravity type angle meter 75 has an indicator needle 76, and the needle 76 provides angle indications relative to markings on the outer case of the angle meter in a conventional manner. The angle meter scale is positioned so the zero line of the scale is aligned with a scribe mark 77 placed on the front cross frame 62, and then the angle meter is cemented into the frame extension 65 to hold it in place and provide a positive, fixed zero for referencing the eyeglass frame assembly 60 during use. When the angle meter 75 reads zero, the cross central axis of the front cross frame is referenced at a horizontal position. The scribe marks 73 and 77 are made to be parallel. Since a fixed zero is two axes during the manufacturing process, this will assure that the same reference points will be indicated for future measurements.

Figure 4:
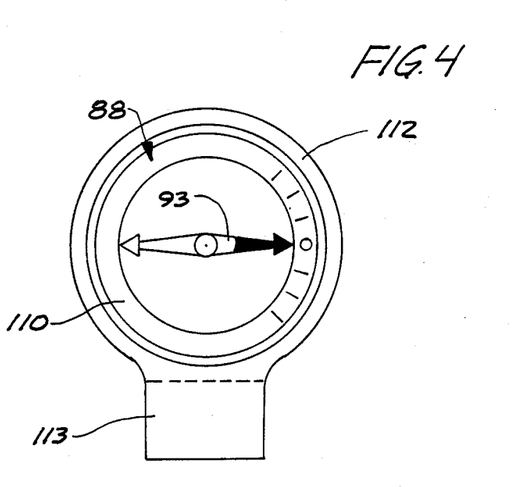
FIG. 4 is a front view drawing of a precision-molded angle finder mount, with a typical magnetic angle finder shown in position thereon.

As stated, the gravity type angle meters utilized are fluid damped to allow measurements to be read quickly and accurately without substantial needle vibration or flutter. Usually, the angular markings scale, as shown in FIG. 4 are plus or minus 110°, and the indications are usually in 2° markings, although that is not illustrated specifically.

Rotation about the cervical axis is measured with a magnetic type angle meter indicated generally at 80 in FIGS. 1 and 2. The magnetic type angle meter assembly 80 includes a mounting arm 81 that has a first vertical portion 82 and a second horizontal portion 83. The vertical portion 82 of the arm is made to slip fit into a slide fit, sleeve type coupling member 84, at the upper end of upright front frame extension 65, and which is centered with respect to a vertical plane passing through the axis of rotation of needle 76 and the reference mark 77. The vertical portion 82 of the arm 81 has a tang member 86 that is reduced in size and which slips into the coupling member 84 to hold the arm assembly 81 in position. A magnetic type angle meter 88 is mounted on arm 81, and is similar to a magnetic compass and has a needle that is magnetized and carries indicia on one end (the darkened end) which will point to magnetic North. The axis of the needle 93 (FIG. 3) is located within a reasonable distance from the cervical rotation axis, which is shown at 90 in FIG. 1. Having the rotational axis of the needle 93 for the magnetic type angle meter 88 within an inch and a half or so of the actual axis 90 of cervical rotation will be satisfactory.

Figure 3:
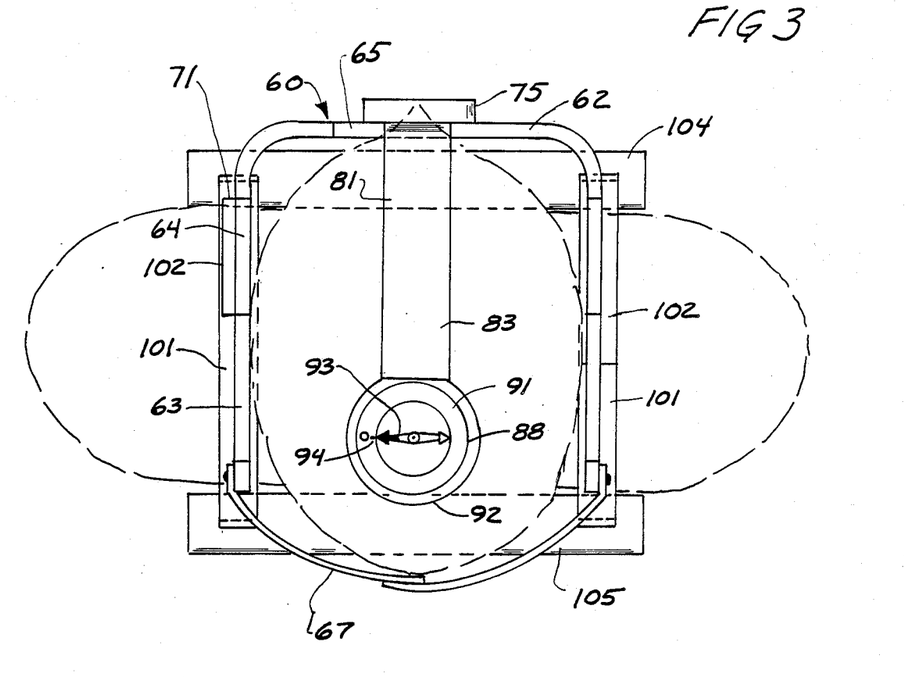
FIG. 3 is a top plan view of the device of the present invention showing a magnetic type angle meter for measuring head rotation.

As can be seen in FIG. 3, the mounting for the magnetic type angle meter 88 is made so that it has an outer case 91 that can be rotated relative to its precision mounting support 92 on the horizontal section 83 of the arm assembly 81. The angle meter case for angle meter 88 can be rotated until the appropriate end of needle 93 (south magnetic pole) is set at a zero marking or indicia on the outer case indicated at 94 in FIG. 3. Adjustments of the cases of such angle measuring devices are well known, and the case is spring loaded so friction causes the case to remain at a setting after being manually adjusted.

The arm assembly 81 is removable from coupling member 84 to allow for complete flexion and extension of the neck in the sagittal plane, when the flexion and extension measurements are being taken, and then the arm assembly 81 can easily be replaced using the precision molded coupling member or socket 84 and the tang portion of the vertical section 82 of arm assembly 81.

It should be noted that the arm assembly 81 can be made with different lengths of the horizontal section 82, to accomodate abnormal neck protrusions or for small children.

In this form of the invention, a magnetic needle 93 of the magnetic type angle meter is placed under the influence of a magnetic field provided in order to eliminate the problem of various unpredictable external magnetic fields and shielding of the earth's magnetic field.

As shown in FIGS. 1 and 2 in particular, the magnetic field alignment device indicated generally at 100 comprises a shoulder harness 101 that includes a pair of adjustable straps 102 which are made in two segments, the straps are supported over the shoulders of a subject and can be adjusted as desired. On both the front and rear of the subject, the straps 102 carry magnet housings 104 and 105, respectively, that are laterally extending belongated housing members that extend in front of the neck and across the back of the neck as shown, and which rest on the body of the subject. The housings 104 and 105 each mount a plurality of separated individual permanent magnets, which are indicated in dotted lines at 106 in FIG. 2. The same type of magnets are positioned in the housing 105, and they are mounted so their North poles will be oriented toward the end indicated by a "North" arrow 110. This is generally done so that the North arrow is pointing in the direction of magnetic North, during operation.

The magnetic field alignment device, once it is mounted on the patient's or subject's shoulders, also provides compensation for inadvertent movement of the shoulders during head rotation because the strongest field from the magnetic field alignment device will follow the shoulders, and provide more reliable indication using magnetic type angle meters. Using a number of individual magnets also makes the harness more flexible, and the housings 104 and 105 can be made of a suitable flexible material if desired. The individual magnets are less likely to break by inadvertent dropping of the magnetic field alignment device as well.

Figure 5:
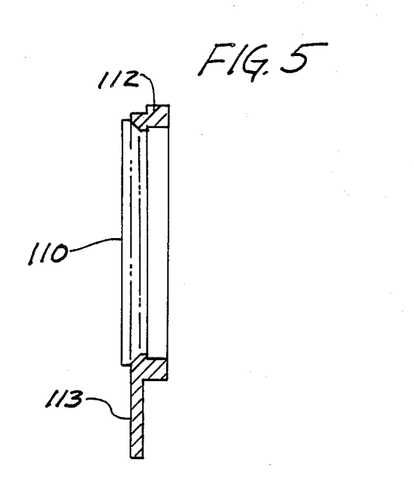
FIG. 5 is a side elevational view of the device of FIG. 4 with the angle meter removed.

FIGS. 4 and 5 illustrate a typical precision molded mount for a goniometer, and in particular the magnetic type angle meter shown at 88 in FIG. 1. However, the angle indicia are the same on gravitational-type angle meters except oriented differently. In this form of the invention, a molded outer ring 112 is made with an interior bore of size to mount an angle meter housing. The ring 112 has a mounting tang 113 that can be bonded to the arm section 82. FIG. 11 shows the mounting ring 112 without the angle meter in place. The gravity angle meters also can be adjustable. The plates shown can be removed and mounts made for the outer cases as shown in FIGS. 4 and 5. The angle meter case can be spring loaded on the frame so spring load friction is developed to retain the angle meter from unwanted movement.

As shown in FIGS. 1, 2 and 3, once the frame assembly 60 is properly mounted on the subject, the measurements in the frontal and sagittal planes can be taken with the arm assembly 81 removed.

The examiner will fasten the adjustable strap 67 in proper position so that the nose pad 61 properly locates the frame assembly 60 and bows on the ears, and retains it at a reference position. The subject will stand facing away from an outside corner of a wall, or from an edge of an open door frame. The sacrum, thoracic spine, and occiput must be in contact with the corner of the wall or door edge in order to provide for a reference posture position of the subject. Since the sagittal plane angle meter 71 reads zero when the bows are parallel to a horizontal plane, the initial angular reading should be recorded as an indication of resting suboccipital posture. The angle meter 71 does not have to be at zero on its scale, but a reference reading can be taken from the angle meter. The suboccipital flexion-extension movements are accomplished by having the subject slide the occiput along the contact surface without changing the pressure.

The subject will move through the maximum range of suboccipital flexion while maintaining equal pressure at the skull, the thorax, and the sacrum, and the measurement from the angle meter 71 is recorded. The subject then can move through a maximum range of suboccipital extension (in the opposite direction from flexion) without allowing the skull or thorax to leave the contact surface, and the measurement of movement is recorded from the angle meter 71.

The subject is then seated in a straight-backed chair, and can be analyzed for cervical flexion and extension measurements. The subject is seated erect in the chair, with the sacrum against the back of the chair, but with the back of the subject slightly away from the back of the chair, and with the subject's arms hanging at the sides. Both feet should be flat on the floor. Since cervical flexion/extension measurements are from multi-joint motions, it is important that the subject be instructed to nod (i.e. nod your head to make a double chin). Upon completion of full suboccipital motion, the subject continues movement until cervical flexion is obtain. Cervical extension is measured in a similar fashion, with suboccipital extension first, which is the "nod your head back" motion followed by cervical spine extension, and then the angle measurement is recorded utilizing the angle meter 71 with the angles being indicated by the needle 72, again with reference to an initial or reference position.

Head rotation measurements can also be taken with the subject seated in a straight-backed chair as described above. The arm assembly 81, and the magnetic type angle meter 88 are put into position, and the magnetic field alignment device or yoke 100 is put into place before the rotation measurements. To obtain maximum accuracy with the head rotation measuring angle meter, which utilizes the magnetic needle 93, initial positioning should be done with the magnetic field alignment device removed from the subject and placed several feet away so the field from magnet 106 has no influence on the needle 93. Then the subject should be positioned so that a line across the subject's shoulders should be lined up with the needle 93 as the end of the needle coded for magnetic North (the darkened end) is indicating magnetic North.

The magnetic field alignment device 100 is then placed over the subject's shoulders with the arrow on the housing pointing to magnetic North, as is shown in FIG. 2.

The sagittal and frontal plane gravity type angle meters, which have the preset zeros, can be then used for referencing the position of the subject's head and both of these indicator needles, namely needles 72 and 76, should be indicating zero. Then the magnetic type angle meter 88 will be level (because of the preset fixed zeros of the gravity type angle meters) so that the magnetic needle 93 will be free to rotate easily.

The angle meter 88 can be set so the darkened end of the needle is at zero, because the outer case 91 can be rotated until the zero setting is aligned with that end of the needle, when the subject is looking straight ahead at a reference position. The subject should focus on a horizontal line on the wall so that the head is not tipped during rotation once the angle meters 71 and 75 indicate a zero (level) setting. To insure that no rotation of the shoulder occurs, the shoulders of the subject can be stabilized by placing a hand on a shoulder of the subject opposite from the direction of rotation. The head of the subject is then first turned to the left and the measurement recorded, and then the head of the subject is rotated to the right and the measurement recorded with magnetic type angle meter 88 to obtain the desired movements. Thus, the measurements of the desired angles of movement in all desired planes can easily be obtained.

Figure 6:
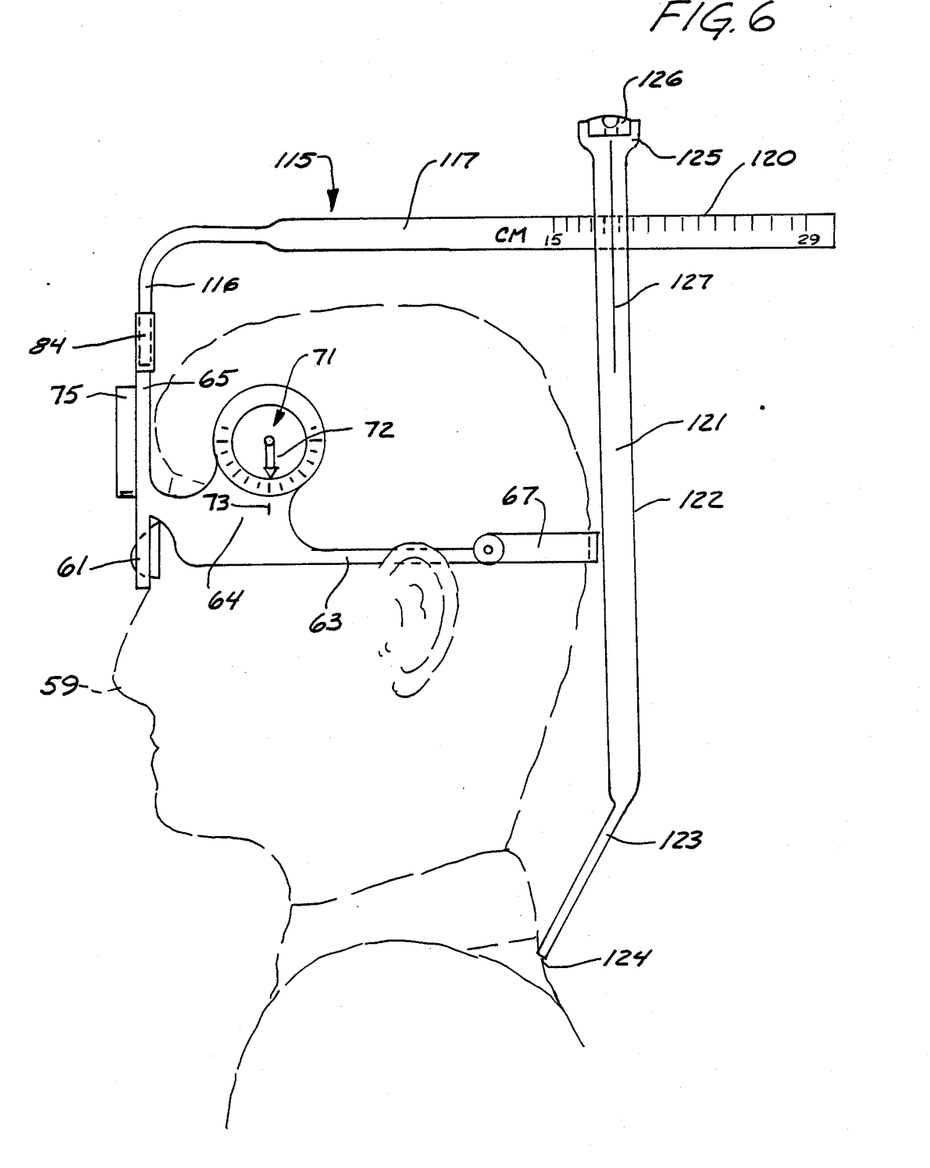
FIG. 6 is a left side elevational view of an alternate embodiment of the invention showing a forward-head position measuring arm and vertabrae locator mounted in place.

In FIG. 6, the frame 60 is shown with the rotational magnetic type angle meter 88 removed, and with a forward head portion measurement device installed. In this form of the invention, the coupling member 84 is used for mounting a calibrated arm assembly 115 that includes a vertical section 116, and a horizontal indicator section 117. The indicator section 117 comprises a blade that is positioned in the vertical plane, so that its flat side is extending up and down, and it has a series of metric scale markings thereon which are indicated at 120.

The vertical section 116 has a tang portion that fits into the coupling member 84 for securely holding the arm assembly 115 is position.

A vertebrae locator bar 121 has a main blade portion 122 that is a flat strap-like blade, and an angled end portion 123 that extends inwardly from the plane of the blade portion 122, and which has a lower end surface 124. This forms a locator or pointer end 124. The upper end of main blade portion 122 of the vertebrae locator bar 121 has a mounting yoke 125 that mounts a bubble level 126 of conventional design, so that it will be known when the central axis indicated at 127 of the main blade portion 122 is vertical.

The locator bar 121 is positioned by the examiner on the seventh cervical vertebrae of the subject, and the angled member 123 is made so that it will clear the back portion of the subject's head. The locator bar 121 can be formed of plastic or other suitable material. Likewise, the arm 115 can be formed of plastic and the indicating indicia or lines 120 are located so that on typical subjects, the indicia 120 will be able to indicate the horizontal distance from the bridge of the nose to the spinous process of the seventh cervical vertebrae. The scale is located so the axis line 127 indicates such distance.

Once the arm 115 is properly positioned, the locator bar 121 is positioned so that the indicator end 124 is touching the seventh cervical vertebrae of the subject and using the bubble level 126 the axis line 127 is positioned to be vertical. Then a reading can be taken from the indicia 120 (which indicates in half-centimeters) to provide a reading of the horizontal forward head position relative the seventh cervical vertabrae.

For taking these measurements, the subject is again seated in a straight-backed chair, in a erect position with the sacrum against the back of the chair, the subject's back positioned slightly away from the back of the chair, the arms hanging down at the subject's sides, and with both feet being flat on the floor. The rotational angle meter 88 and the magnetic field alignment device are both removed during the forward head position measurements, because the arm 115 has to be positioned on the frame as explained.

The examiner will stand to the subject's left enabling a reading of the sagittal plane gravity type angle meter 71 shown in FIG. 6. Then the examiner will assist the subject to position the subject's head so the needle 72 reads zero, to level the head.

The examiner locates the seventh cervical vertebrae and places the bottom indicator end 124 in this manually located position. The locator bar 121 is then moved so that the bubble in he bubble level 126 is centered assuring that the axis line 127 will be vertical, and after making sure that the sagittal angle meter 71 is still at zero, the measurement can be taken from the indicia 120 and recorded. This will give the forward head portion measurement, and can be used for analysis. The portion of the angle meter 71 at the left temple makes it easily visible for an examiner using the right hand to manipulate the locator bar 121.

Additional measurements, such as a rounded shoulder measurement can be taken of the subject using a flexible ruler to complete the postural profile of the subject.

Thus, the necessary angles of movement of the head can easily be obtained, and the device can be used for determining forward head position measurements, as explained.

Although the present invention has been described with reference to preferred embodiments, workers skilled in the art will recognize that changes may be made in form and detail without departing from the spirit and scope of the invention.

What is claimed is:

1. An apparatus for measuring the range of cervical motion about at least two axes of rotation including:
   a frame for detachably mounting the apparatus to a human head, said frame having a nose pad adapted to be supported on the bridge of the nose as a reference location and as a support for the frame, and temple pieces adapted to be positioned on opposite sides of a head and to rest on the top exterior of each ear for supporting and stabilizing the frame on the head of a wearer;
   first angle meter means mounted on said frame for determining changes in angles about a first axis;
   second magnetic type angle meter means adapted to be supported relative to the frame for determination of changes in angles of rotation about a second upright axis substantially perpendicular to the first axis and relative to a magnetic pole;
   means mounted on the frame for mounting the second magnetic type angle meter means in a position adapted to overlie the head of a subject wearing the frame adjacent the axis of cervical rotation of such subject and without acting as a support for the frame; and
   a magnetic field creating device means adapted to be mounted on such subject at a location spaced from the second magnetic type angle meter means, said magnetic field creating device means creating a magnetic field having a north magnetic pole for controlling orientation of the needle of the second magnetic type angle meter means.

2. The apparatus according to claim 1 wherein said first angle meter means comprises a pendulum mounted about the first axis, said first axis being substantially horizontal in use.

3. The apparatus according to claim 2 wherein the first angle meter means is mounted on the frame adjacent the nose pad and measures angles in a frontal plane.

4. The apparatus according to claim 1 wherein said second angle meter means has a rotatable face for zeroing the reading and has an angular scale marked thereon.

5. The apparatus according to claim 1 wherein the first angle meter means comprises a gravity type angle meter mounted on a side of said frame to measure angles in the sagittal plane of movement of a head of a subject wearing the frame.

6. The apparatus as specified in claim 1 wherein said magnetic field creating device comprises a harness having support straps for mounting over the shoulders of a subject wearing the frame and comprising magnets adapted to be positioned on both front and rear portions of such subject.

7. The apparatus as specified in claim 1, wherein said frame is a molded plastic frame, and strap means to retain the temple pieces on the head of a subject wearing the frame, which strap means is adapted to extend around the back of the head of such subject.

8. The apparatus according to claim 1 and a third gravity type angle meter mounted on the frame and positioned to measure angles about a third axis mutually perpendicular to the first and second axes and wherein the first and third angle meter means have outer cases which are fixed to the frame in a reference position adjacent fixed zero marks and perpendicular to each other to provide known reference positions for the angle meter means and to provide means for leveling the frame when using the magnetic angle meter means for measuring rotation about the cervical axis.

9. The apparatus as specified in claim 1 wherein the means for mounting the second magnetic type angle meter means comprises a removable arm having a first upwardly extending portion mounted to the frame above the nose pad and a second portion that is adapted to extend generally horizontally above the head of a subject wearing the frame without acting as a support for the frame.

10. The apparatus of claim 9 and a second arm adapted to be mounted in place of the first mentioned arm, which second arm has a first upwardly extending portion mounted on the frame above the nose pad, said second arm having a second horizontal portion adapted to be above the head of a subject wearing the frame and extending rearwardly, the horizontal portion having indicia thereon that indicates that distances from the forward portion of the head of a subject wearing the frame, and means for providing a reference indication with respect to a desired portion of the spine of a subject wearing the frame relative to the forward portion of the head of such subject.

11. An apparatus for evaluating cervical functions of a subject comprising:

a frame mountable on a head, said frame having a nose pad adapted to be supported on the bridge of the nose of a head as a reference and as a support for the frame, and temple pieces adapted to be positioned on opposite sides of a head and resting on ears of such head for stabilizing the frame on the head of a wearer of the frame;

a mounting arm, said mounting arm being mounted on the frame adjacent the nose pad and including a first arm portion extending upwardly from the nose pad, and a second arm portion that extends substantially horizontally and is adapted to overlie the head of a wearer of the frame without acting as a support for the frame;

indicating means carried by said second horizontal portion of the mounting arm and adapted to be above the head of such wearer for providing indications of cervical functions of a wearer of the frame, said indicating means comprising indicia that indicates distances from the forward portion of the head of a wearer of the frame; and means adapted for locating a reference with respect to a desired portion of the spine of a wearer of the frame relative to the forward portion of the head of such wearer and for cooperating with the indicia on the indicating means to provide a distance measurement related to the mounting of the mounting arm on the frame.

12. The apparatus of claim 11 wherein the means adapted for locating a reference comprises an elongated locator bar having a first end adapted for engaging a portion of the spine of such wearer and having an elongated portion extending upwardly to cross at least a portion of the indicia for providing a position indication.

13. The apparatus of claim 12 and a level indicator on the locator bar for indicating when the elongated portion is at a known orientation relative to a vertical axis.

14. The apparatus as specified in claim 11 wherein said indicating means comprises a magnetic type angle meter mounted on said horizontal portion of the arm, and having a needle for indicating a direction to a selected magnetic pole of a magnetic field, the needle being mounted for movement to indicate rotation of the frame about a cervical rotational axis of a wearer of the frame.

15. A system for measuring the range of cervical motion about at least the axis of cervical rotation of the head of a subject including:

a frame mountable on a human head, said frame having a nose pad adapted to be supported on the bridge of the nose of a subject, and temple pieces adapted to be positioned on opposite sides supported on ears of the head of a subject;

magnetic type angle meter means supported by said frame and positioned so as to be above the head of a subject wearing the frame so that said angle meter means indicates angles of movement about the cervical axis;

reference magnetic field means for creating a magnetic field, having a north magnetic pole which influences the magnetic type angle meter means and provides a reference position for the magnetic type angle meter means; and means for supporting the reference magnetic field means on a subject wearing the frame at a location spaced from the magnetic type angle meter means.

16. The apparatus of claim 15 wherein the magnetic type angle meter means is mounted on a mounting arm, said mounting arm including a first portion removably mounted on a forward portion of the frame and extending upwardly, the mounting arm having a second portion that extends substantially horizontally and will overlie the head of a subject wearing the frame, and means for supporting the magnetic type angle meter means on the horizontal portion.

17. The apparatus as specified in claim 15 wherein said means for supporting the reference magnetic field means comprises a shoulder harness that is adapted for mounting on the shoulders of a subject wearing the frame.

18. The apparatus of claim 17 wherein the reference magnetic field means comprises a permanent magnet having north and south poles which are adapted to be carried in the harness along a line generally corresponding to a line across the shoulders of such subject.

19. The apparatus as specified in claim 15 wherein said frame is a molded plastic frame, and strap means to retain the temple pieces on the head of a subject wearing the frame, which strap means is adapted to extend around the back of the head of such subject.

20. A method of determining forward head position of a subject relative to a reference position of the spine of a subject comprising the steps of:

positioning an arm above the head of a subject referenced to a known location at the forehead of a subject and extending generally horizontally to the rear of the head of said subject;

said arm having indicia thereon indicating distance to the known location at the forehead of said subject;

positioning a first end of a locator bar at the reference position of the spine of said subject, said locator bar having an elongated portion extending upwardly across a portion of the arm at the rear of the head of said subject;

orienting the upwardly extending elongated portion of the locator bar along a reference axis with the first end of the locator bar at the reference position of the spine of said subject; and reading the distance indicated on the arm where the upwardly extending elongated portion of the locator bar crosses the arm.

21. The method of claim 20 including the step of positioning the arm on a frame and supporting the frame relative to the bridge of the nose and the ears of the subject.

22. The method of claim 21 including the step of orienting the frame relative to a horizontal plane by providing a gravity type angle meter on the frame with a fixed reference position indicator cooperating with the angle meter.

* * * * *